Figure 1:
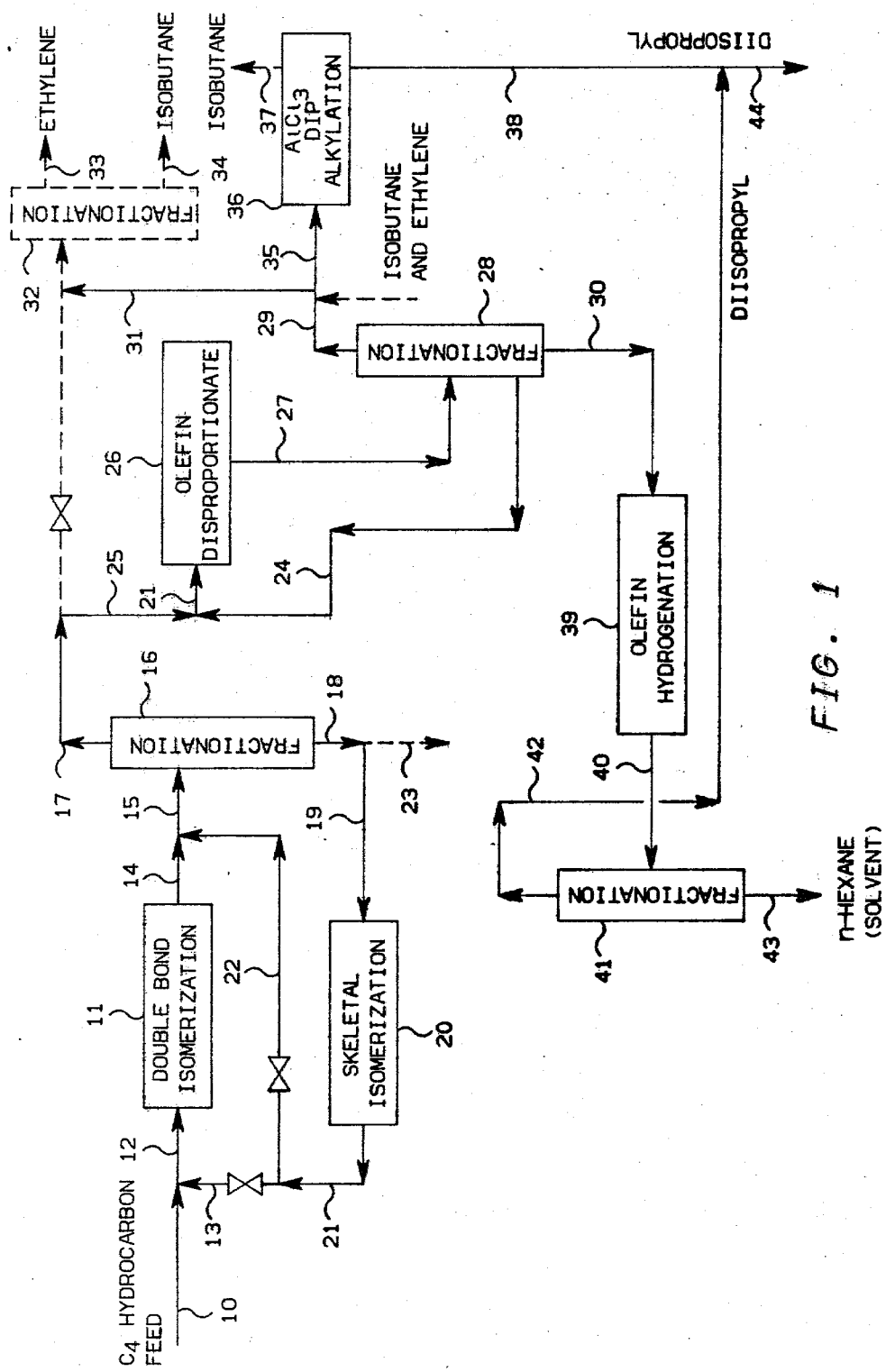

United States Patent [19]

Dixon

[11] 4,255,605
[45] Mar. 10, 1981

[54] DIISOPROPYL FROM BUTENES

[75] Inventor: Rolland E. Dixon, Bartlesville, Okla.

[73] Assignee: Philliphs Petroleum Company, Bartlesville, Okla.

[21] Appl. No.: 108,995

[22] Filed: Jan. 2, 1980

[51] Int. Cl.$^3$ .............................................. C07C 2/58
[52] U.S. Cl. ................................... 585/332; 585/324; 585/326; 585/329; 585/331; 585/644; 585/264; 585/709
[58] Field of Search ............... 585/324, 326, 329, 644; 585/264, 332, 331, 709

[56] References Cited

U.S. PATENT DOCUMENTS

| | | | |
|---|---|---|---|
| 3,113,986 | 12/1963 | Breslow et al. | 585/266 |
| 3,321,547 | 5/1967 | Banks | 585/324 |
| 3,660,517 | 5/1972 | Reusser et al. | 585/644 |
| 3,723,562 | 3/1973 | Hecklesberg | 585/324 |
| 3,729,524 | 4/1973 | Reusser | 585/329 |
| 3,754,052 | 8/1973 | Hoffman et al. | 585/332 |
| 3,763,261 | 10/1973 | Sobel | 585/332 |
| 3,767,565 | 10/1973 | Banks | 585/332 |
| 3,785,956 | 1/1974 | Banks | 585/324 |
| 3,793,393 | 2/1974 | Neal | 585/332 |
| 4,085,158 | 4/1978 | Dixon et al. | 585/326 |
| 4,176,141 | 11/1979 | Dixon | 585/324 |
| 4,191,845 | 3/1980 | Rubin et al. | 585/324 |

Primary Examiner—Veronica O'Keefe

[57] ABSTRACT

A process for producing high octane DIP (2,3-dimethylbutane) from mixed $C_4$ olefins comprising the steps of subjecting the mixed $C_4$ olefines to double bond isomerization, skeletal isomerization, olefin disproportionation, olefin hydrogenation and fractionation to yield DIP.

13 Claims, 2 Drawing Figures

DIISOPROPYL FROM BUTENES

This invention relates to hydrocarbon conversion. In another aspect, this invention relates to the production of diisopropyl (2,3-dimethylbutane) from mixed $C_4$ olefins. In accordance with another aspect, this invention relates to a combination process for converting mixed butenes to high octane diisopropyl (DIP) in a combination of steps including double bond isomerization, skeletal isomerization, olefin disproportionation (Triolefin reaction), olefin hydrogenation and fractionation to yield a number of product streams including DIP.

Accordingly, an object of this invention is to provide an improved process for the production of high octane DIP.

A further object of this invention is to provide an improved process for the conversion of mixed olefins to more valuable products.

A further object of this invention is to provide a combination process for yielding separate streams of valuable products.

Other objects, apsects, and the several advantages of this invention will become apparent to one skilled in the art upon the study of this disclosure, the drawings, and the appended claims.

In accordance with the invention, there is now provided a process for producing high octane DIP (2,3-dimethylbutane) from mixed $C_4$ olefins comprising the steps of subjecting the mixed $C_4$ olefins to double bond isomerization, skeletal isomerization, olefin disproportionation, olefin hydrogenation and fractionation to yield DIP.

More specifically, in accordance with the invention a combination process is provided for the production of diisopropyl (DIP) from a mixed butenes feedstream comprising butene-1, butenes-2, isobutane, n-butane and isobutylene (isobutene) wherein the process comprises the combination of steps (a) double bond isomerization of butene-1 to butenes-2, (b) skeletal isomerization of butenes-2 to isobutylene (c) olefin disproportionation to convert isobutylene to ethylene and 2,3-dimethylbutene-2 and butenes-2 to ethylene and normal hexene and heavier olefinic hydrocarbons, (d) olefin hydrogenation of 2,3-dimethylbutene-2 to 2,3-dimethylbutane (DIP) and (e) fractionation of the effluent from the double bond isomerization, the olefin disproportionation and the olefin hydrogenation yielding a number of different individual products from the process.

The double bond isomerization, the skeletal isomerization, the olefin disproportionation (triolefin reaction), and olefin hydrogenation reactions are known in the art. In accordance with this invention, these known processes have been matched in a manner to produce diisopropyl from mixed $C_4$ olefins. The effluents from the various reactions in this invention have to be separated in separation zones. All of these separation zones comprise generally several individual separating units such as fractionation towers, absorber strippers, etc. These units will be explained in some detail in connection with the drawing. It has to be emphasized, however, that the separation actually achieved can be achieved in various manners, and the invention should not be unduly limited to the specific manners in which these separations are shown in the drawings.

Butene-1 Double Bond Isomerization

One convenient method of converting butene-1 by double bond isomerization or hydroisomerization to butene-2 is by contacting the butene-1 with a catalyst comprising ruthenium oxide. Ruthenium oxide is associated with a suitable support material. Preferred supports include silica, silica-alumina, alumina, and titania. Excellent results are obtained when the support is silica. When the catalyst support is silica, any suitable catalyst grade silica can be employed. Some examples are precipitated silica gel microspheroidal silica, flame hydrolyzed silica, and silica aerogels. These materials have appreciable surface area, usually in the range of about 50 to 700 $m^3/g$, and can range from fine powders to coarse granules. These materials often contain small amounts of other compounds, including, for example, amounts of alumina and sodium in the order of a few tenths of a percent by weight and smaller. Amounts of these and other materials which do not substantially prevent the desired reaction or unduly promote side reactions are acceptable.

A sufficient amount of the ruthenium oxide is used to obtain the desired activity. Because ruthenium oxide usually is more expensive than the support material, unnecessary large amounts ordinarily are not used. Generally, the catalyst composite contains the 1 to 15, preferably about 2 to 10, weight percent ruthenium oxide calculated as $RuO_2$, and can be prepared by any suitable method of catalyst preparation, preferably by impregnation. Before use, the catalyst composite can be activated or regenerated by contact with flowing air at elevated temperatures at a time sufficient to produce the desired activity. Activation temperatures in the range of about 800° to 1200° F., for times ranging from about 0.1 to 24 hours, are suitable.

Exemplary conversion temperatures lie in the range of about 200° to 700° F., at any suitable pressure, preferably temperatures in the range of about 300° to 600° F. Pressures in the range of about 0 to 2,000 psig, for example, can be used. The space rate for continuous operation usually will be in the range of about 5 to 15 parts by weight of feed per part by weight of catalyst per hour. After reaction, the reaction mixture can be separated as desired, and unconverted materials recycled to the reaction zone.

The process can be carried out by any suitable contacting techique, either batchwise or continuously, using such as a fixed catalyst bed, stirrer equipped reactor, or other mobile catalyst contacting process.

Butenes-2 Skeletal Isomerization

When it is desired to convert all or a portion of the butenes-2 by skeletal isomerization to isobutene, any means known to the skeletal isomerization arts can be employed. One convenient means for converting butenes-2 to isobutene employs an activated catalyst of zirconium oxide, or compound convertible to zirconium oxide upon calcination, preferably promoted by a halogen compound. A presently preferred example can be represented by $ZrOX_2$ wherein X is fluoride, bromide, chloride, or iodide, on alumina. Of these, presently the zirconyl chloride is more preferred. Of the aluminas, presently preferred are eta- and gamma-alumina, and presently most preferred is eta-alumina. A suitable and exemplary catalyst can be prepared by incorporating about 0.4 to 15 weight percent, preferably about 1 to 10 weight percent, based on the total composition, of zirconyl halide into the selected alumina, such as by impregnating a dried and calcined alumina with an aqueous solution of the desird zirconyl halide, followed by calcination at suitable temperatures such as about 500° F. to 1200° F. for a time such as about 0.1 to 25 hours, in air, or other gas such as nitrogen.

The skeletal isomerization step can be carried out by contacting the feed with catalyst, using any suitable contacting techniques, at a suitable temperature at which skeletal isomerization of the feed olefin will occur. The temperature preferably is in the range of about 400° to 1200° F. or more, preferably about 600° to 1100° F. The liquid hourly spacce rate generally will be in the range of about 0.1 to 50, preferably about 0.5 to 30. Any convenient pressure can be used, with the lowest practical pressure preferred in order to minimize side reactions such as polymerization. Pressures ranging from atmospheric to such as about 200 psig are particularly suitable.

Disproportionation

Triolefin Reaction

In the disproportiontion steps of the instant process, the basic reaction is to convert an olefin in the feed to higher and lower molecular weight olefins. The disproportionation reaction is sometimes also generically referred to as the Triolefin process although there are generally more than three olefins involved in the process. In one embodiment of the invention, an effluent from the hydroisomerization unit is passed to a disproportionation zone also referred herein as a butenes-2 cleavage zone wherein butenes-2 are converted to propylene in the presence of ethylene. In another embodiment, a propylene-rich stream separated from the effluent of the butenes-2 cleavage zone is subjected to disproportionation to produce ethylene and butenes-2. In still another embodiment, a stream comprising isobutane, isobutylene, and some normal butene is charged to a disproportionation zone wherein isobutylene and propylene react to produce DIP and ethylene.

The disproportionation sometimes is termed the "olefin reaction" which can be visualized as comprising the reaction between two first pairs of carbon atoms, the two carbon atoms of each first pair being connected by olefinic double bond, to form two new pairs from the carbon atoms of said first pairs, the two carbon atoms of each of said two new pairs being connected by an olefinic double bond.

Among the suitable catalysts are silica or thoria promoted by an oxide, or a compound convertible to the oxide by calcination, of tungsten, molybdenum, rhenium, or tellurium, or by a sulfide of tungsten or of molybdenum.

Other suitable catalyst include aluminum phosphate, zirconium phosphate, calcium phosphate, magnesium phosphate, or titanium phosphate, promoted by one or more of a sulfide of molybdenum or tungsten, or by an oxide or of a compound convertible to the oxide on calcination, of molybdenum, tungsten, or rhenium, or by magnesium tungstate or beryllium phosphotungstate. These catalysts can be in the form of a powder or granules, as well as a variety of other shapes as is known in the art.

With a fixed bed reactor means in a continuous operation mode, temperatures presently preferred are in the range of about 650 to 850° F., employing a pressure in the range of about 100 to 350 psig, employing a weight hourly space velocity in the range of about 50 to 200, preferably about 75 to 100, weight/weight/hour.

Olefin Hydrogenation

The hydrogenation amount is operated under any of the conventional operating conditions with any of the commercially available catalysts. A typical hydrogenation of 2,3-dimethylbutene-2 to DIP using a fixed bed of nickel on alumina having 40 weight percent nickel in the total mass:

|  | Range | Specific |
|---|---|---|
| Pressure, psia | 250 to 350 | 300 |
| Inlet Temp., °F. | 75 to 150 | 100 |
| Outlet Temp., °F. | 175 to 250 | 200[a] |
| Liquid Vol/Vol Cat/hr. | 2 to 6 | 4 |
| H$_2$/Olefin Mol Ratio | 1 to 1 to 1.5 to 1 | 1.1 to 1 |

[a]Maintained by recycle of cooled hydrogenated product. (Total feed has about 10 percent olefin.)

Figure 2:
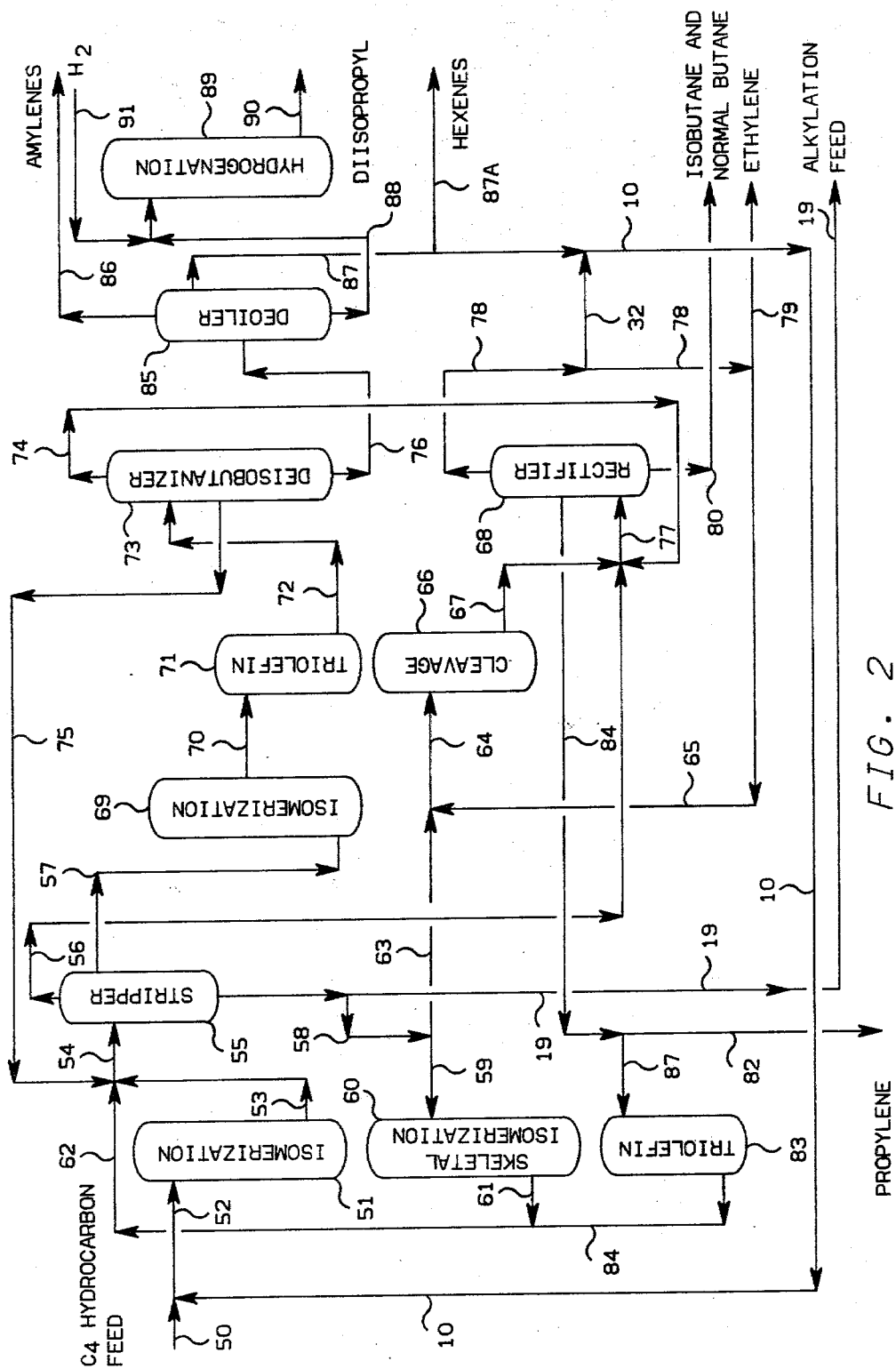

Further details and preferred embodiments of this invention will become apparent to those skilled in the art from the following description of the drawings in which FIG. 1 present a schematic overview of the process including several of the optional but desirable recycle and conversion steps and FIG. 2 is a view including a more detailed flow and to some extent different combination of steps from FIG. 1.

Both FIGS. 1 and 2 set forth a combination of conventional processes to convert a butylenes feedstream into ultimately isobutylene and the isobutylene produced, along with isobutene in the butenes feedstream is subjected to disproportionation to produce 2,3-dimethylbutene-2 and the resulting 2,3-dimethylbutene-2 is hydrogenated to produce a high octane DIP (2,3-dimethylbutane).

Referring now to FIG. 1, a butylenes-butane feedstream 10 comprising isobutane, normal butane, butene-1, butenes-2 and isobutylene is charged to double bond isomerization zone 11 by way of line 12 wherein butene-1 is isomerized to butenes-2. If desired, a subsequently produced butylenes-butane stream 13 comprising isobutene, butenes-2 and normal butane is charged to double bond isomerization zone 11 along with feed 10. An effluent stream 14 removed from zone 11 is passed by way of line 15 to fractionation zone 16 which is operated under conditons to remove overhead by line 17, a stream comprising isobutane, isobutene, and lighter hydrocarbons and a bottoms stream 18 comprising normal butane and butenes-2.

A portion of bottoms stream 18 is passed by way of line 19 and introduced into skeletal isomerization zone 20 wherein butene-2 are converted to isobutylene. The effluent removed from isomerization zone 20 by way of line 21 is preferably passed by way of line 22 and combined with the effluent from zone 11 for introduction into fractionation zone 16. As indicated above, the effluent from zone 20 can be passed in part or in toto as part of the feed to zone 11 or fractionation zone 16.

Fractionation Zones

Conventional fractionation is employed. A fractionation zone, as illustrated, can be one or more fractionation columns. The temperatures selected, of course, depend on the pressures selected and the composition of the separations which are to be made, as is known by those skilled in the fractionation art.

Typical operating conditons for fractionation zone 16 include a suggested top temperature of about 140° F., a bottom temperature of about 160° F., and an operating pressure of about 120 psia.

A portion of bottoms stream 18 can be removed from the system by line 23 to prevent normal butane build-up in the process. Stream 23 is preferably charged to an HF alkylation to alkylate isobutane to high octane butylenes alkylate.

Overhead 17 removed from fraction zone 16 along with a butylenes containing stream 24 subsequently recovered is passed by way of line 25 to olefin disproportionation zone 26 wherein isobutylene yields ehtylene and 2,3-dimethylbuene-2 and butenes-2 yield ethylene and normal hexene plus unavoidably some hevier olefinic hydrocarbons. The effluent from zone 26 is passed by way of line 27 to fractionation zone 28 operated under conditoins as to remove overhead ethylene and isobutane by line 29 and as bottoms 2,3-dimethylbutene-2, hexenes and heavier by line 30.

Typical operating conditions for fractionation zone 28 include a suggested top temperature of about 140° F., a bottom temperature of about 350° F., and an operating pressure of about 170 psia.

Overhead 29 comprising ethylene and isobutane can, in part, be passed by way of line 31 to fractionation zone 32 to yield ethylene in line 33 and isobutane in line 34. The isobutane can be used in HF alkylation. At least a portion of overhead 29 is passed by way of line 35 to DIP alkylation zone 36 which includes fractionation facilities. Any excess isobutane can be recovered by line 37 and DIP is recovered by line 38.

The 2,3-dimethylbutene-2-rich bottoms stream 30 removed from fractionation 28 is passed to olefin hydrogenation to produce 2,3-dimethylbutane (DIP) in olefin hydrogenation zone 39. Effluent 40 comprising normal hexene and 2,3-dimethylbutane (DIP) is passed to fractionation zone 41 wherein DIP is taken overhead as product by way of line 42 and normal hexane as bottoms by way of line 43. The DIP recovered in line 42 can be combined with DIP in line 38 and passed by line 44 for further use as desired.

Typical operating conditons for fractionation zone 41 include a suggested top temperature of about 240° F., a bottom temperature of about 310° F., and an operating pressure of about 50 psia.

Referring now to FIG. 2, a butylenes feedstream 50 as from a catalytic cracking operation comprising isobutane the desired isobutylene, butene-1, normal butane and butenes-2 is passed to conventional double bond hydroisomerization zone 51 by line 52 to increase the content of butenes-2 therein produced from the butene-1 present and recovered as stream 53. Isomerization effluent 53 along with other streams to be described hereinbelow is passed by way of line 54 to fractionation or stripping unit 55 to yield three fractions. Stripper 55 is operated under conditions so as to remove an overhead comprising propylene and ethylene by line 56, a side stream rich in butylene by way of line 57 and a bottom stream rich in butenes-2 by way of line 58.

Bottoms stream 58 is charged in part by way of line 59 to olefin skeletal isomerization 60 wherein additional isobutylene is produced from butenes-2. Small amounts of butene-1 are also produced in zone 60. The effluent 61 from zone 60 is passed by way of line 62 and 54 to stripper 55 as previously described.

A portion of bottoms 58 is passed by way of lines 63 and 64 along with ethylene introduced by line 65 to a conventional cleavage zone 66 or olefin reaction zone (triolefin reaction) wherein butene-2 and ethylene produce propylene. The product from zone 66 is passed by line 67 to a rectifier 68 to be described hereinbelow.

Side stream 57 removed from stripper 55 and comprising butene-1 is passed to double bond isomerization zone 69 operated under hydroisomerization conditions such as to convert butene-1 to additional butenes-2. The effluent 70 removed from zone 69 which is rich in isobutylene and lean in butene-1 is passed to olefin-reaction zone 71 wherein isobutylene is converted to the desired 2,3-dimehtylbutene-2 which is removed from zone 71 by line 72 and introduced as the feed for deisobutanizer 73.

Deisobutanizer 73 is operated under conditions sufficient to remove an overhead stream 74 comprising ethylene and propylene, a side stream 75 rich in isobutylene which is recycled to stripper 55 and a bottoms stream 76 comprising 2,3-dimethylbutene-2 and other olefinic hydrocarbons.

As indicated above, streams 56, 67 and 74 are passed to rectifier 68 (fractionation) by line 77 wherein the feed is separated into three fractions comprising an overhead 78 comprising ethylene which, in part, is yielded by line 79 and, in part, charged by line 65 to cleavage zone 66 as previously described. The bottoms stream 80 removed from zone 68 comprises isobutane and normal butane which can be passed to an alkylation (not shown). A side cut 81 comprising propylene which, in part, is yielded in line 82 is passed to olefin reaction 83 wherein the propylene is converted into ethylene and additional butenes-2 which is desired for ultimate conversion to additional isobutylene. The effluent removed from zone 83 by line 84 is passed to stripper 55 for separation.

Bottoms stream 76 removed from deisobutanizer 73 which contains the desired 2,3-dimethylbutene-2 and also small amounts of butenes-2 and hexenes-3,2-methylpentene-2 and 2-methylbutene-2 is passed to deoiler 85 (fractionation). Deoiler 85 is operated under conditions to yield overhead by line 86 pentenes-2 and 2-methylbutene-2, a side cut 87 comprising 2-methylpentene-2 and hexenes-3, a yield stream 87A of hexenes product, and a bottoms stream 88 comprising the desired 2,3-dimethylbutene-2. The bottoms stream 88 is hydrogenated in olefin hydrogenation zone 89 to the desired high octane 2,3-dimethylbutane (DIP or diisopropyl) which is removed as product by line 90. Hydrogen required in zone 89 is introduced by line 91.

Stripper 55, rectifier 68, deisobutanzier 73, and deoiler 85 are conventional separation units. Stripper 55 is a convenient and presently preferred operation mode employs a top temperature of about 140° F., a bottom temperature of about 160° F., and an operating pressure of about 120 psia. In the rectifier, the typical operating conditions include a top temperature of about 50° F., a bottom temperature of about 265° F., and an operating pressure of about 500 psia. In the deisobutanizer, the typical operating conditions include a top temperature of about 140° F., a bottom temperature of about 160° F., and an operating pressure of about 120 psia. In the deoiler, the typical operating conditions include a top temperature of about 125° F., a bottom temperature of about 175° F., and an operating pressure of about 30 psia.

The operations for catalytic reactions in zones 51, 69; 60; 66, 71, 83; and hydrogenation 89 are also well known in the art. The best mode of operation in this invention, temperature and pressure are given below.

|  | Average Temperature °F. | Pressure psig |
|---|---|---|
| Zones 51 and 69 | 450 | 1000 |
| Zone 60 | 850 | 100 |
| Zones 66, 71, 83 | 750 | 225 |
| Hydrogenation 89 | 150 | 300 |

The following calculated example is given to further illustrate the invention and is not intended to limit the scope thereof. This example shows the calculated material balance for the conversion of mixed $C_4$ olefins to 2,3-dimethylbutane. The numerals of the various stream zones in the following table refer to the reference numerals of the corresponding stream in FIG. 2. The calculated example is based on a feed of 388 metric tons/day.

| | Metric Tons/Day | | | | | | | | | | | | |
|---|---|---|---|---|---|---|---|---|---|---|---|---|---|
| | $(50)^a$ | (53) | (54) | (57) | (56) | (58) | (70) | (72) | (75) | (74) | (76) | (86) | (88) |
| Hydrogen | — | — | — | — | — | — | — | — | — | — | — | — | — |
| Ethylene | — | — | 16 | — | 16 | — | — | 27 | — | 27 | — | — | — |
| Propylene | — | — | 83 | — | 83 | — | — | 18 | — | 18 | — | — | — |
| Isobutane | 133 | 133 | 138 | 135 | — | 3 | 135 | 135 | 3 | 132 | — | — | — |
| Isobutylene | 64 | 64 | 294 | 280 | — | 14 | 280 | 154 | 146 | 8 | — | — | — |
| Butene-1 | 53 | 3 | 52 | 49 | — | 3 | 5 | 3 | 3 | — | — | — | — |
| Normal Butane | 40 | 40 | 384 | 19 | — | 365 | 19 | 19 | 19 | — | — | — | — |
| Butenes-2 | 98 | 148 | 343 | 14 | — | 329 | 58 | 31 | 31 | — | — | — | — |
| 2,3, Dimethyl Butene-2 | — | — | — | — | — | — | — | 77 | — | — | 77 | — | 77 |
| Diisopropyl | — | — | — | — | — | — | — | — | — | — | — | — | — |
| Pentenes-2 | — | — | 11 | — | — | 11 | — | 1 | — | — | 1 | 1 | — |
| 2 Methyl Butene-2 | — | — | — | — | — | — | — | 31 | — | — | 31 | 31 | — |
| 2 Methyl Pentene-2 | — | — | — | — | — | — | — | 3 | — | — | 3 | — | — |
| Hexenes-3 | — | — | — | — | — | — | — | 1 | — | — | 1 | — | — |
| Total | 388 | 388 | 1321 | 497 | 99 | 725 | 497 | 497 | 202 | 185 | 113 | 32 | $77^b$ |
| | (90) | (87) | (59) | (63) | (61) | (64) | (67) | (77) | (78) | (80) | (82) | (81) | (84) |
| Hydrogen | — | — | — | — | — | — | — | — | — | — | — | — | — |
| Ethylene | — | — | — | — | 4 | 89 | 76 | 119 | 119 | — | — | — | 12 |
| Propylene | — | — | — | — | 4 | — | 49 | 150 | — | — | 69 | 81 | 44 |
| Isobutane | — | — | 2 | 1 | 2 | 1 | 1 | 133 | — | 133 | — | — | — |
| Isobutylene | — | — | 13 | 1 | 97 | 1 | 1 | 9 | — | 9 | — | — | — |
| Butene-1 | — | — | 3 | — | 55 | — | 1 | 1 | — | 1 | — | — | — |
| Normal Butane | — | — | 325 | 40 | 325 | 40 | 40 | 40 | — | 40 | — | — | — |
| Butenes-2 | — | — | 293 | 36 | 139 | 36 | — | — | — | — | — | — | 25 |
| 2,3, Dimethyl Butene-2 | — | — | — | — | — | — | — | — | — | — | — | — | — |
| Diisopropyl | 79 | — | — | — | — | — | — | — | — | — | — | — | — |
| Pentenes-2 | — | — | 10 | 1 | 11 | 1 | — | — | — | — | — | — | — |
| 2 Methyl Butene-2 | — | — | — | — | 9 | — | — | — | — | — | — | — | — |
| 2 Methyl Pentene-2 | — | 3 | — | — | — | — | — | — | — | — | — | — | — |
| Hexenes-3 | — | 1 | — | — | — | — | — | — | — | — | — | — | — |
| Total | $79^b$ | 4 | 646 | 79 | 646 | 168 | 168 | 452 | 119 | 183 | $69^c$ | 81 | 81 |

$^a$(2) is same as (1); (10) is zero; (32) is zero
$^b$H$_2$ 91 not reported in data
$^c$It is possible to convert all $C_3^=$ to heavier products but the recycle requirements are punitive. $C_3 \rightarrow C_4^= - 2 + C_2^=$, and $C_4^= - 2$ is slowly isomerized to $iC_4^{=2}$ or reconverted back to $C_3^=$, etc.
Calculated example - balance within 1%

I claim:

1. A process of preparation of high octane diisopropyl (2,3-dimethylbutane) from a mixed butenes feed stream comprising butene-1, butenes-2, isobutane, n-butane and isobutylene (isobutene) wherein said process comprises the steps (a) subjecting said mixed butenes stream to double bond isomerization to convert butene-1 to butenes-2;

(b) fractionating the effluent from step (a) into an overhead comprising isobutane, isobutene and butene-1 and a bottoms stream comprising n-butane and butenes-2;

(c) subjecting at least a portion of said bottoms stream in (b) to skeletal isomerization to convert butenes-2 to isobutylene;

(d) combining the effluent from (c) with the effluent from (a) and fractionating the combined streams in (b);

(e) disproportionating the overhead in step (b) to convert isobutylene to ethylene and 2,3-dimethylbutene-2 and butenes-2 to ethylene and normal hexene and heavier olefinic hydrocarbons;

(f) fractionating the effluent from (e) into an overhead comprising $C_2$ and isobutane, a side stream comprising butylenes, and a bottoms stream comprising six carbon hydrocarbons including 2,3-diemthylbutene-2 and n-hexane and heavies;

(g) recycling said sidestream separated in (f) to step (e) for disproportionation;

(h) hydrogenating said bottoms stream separated in (f) to produce n-hexane and 2,3-dimethylbutane (DIP), and (i) a separating 2,3-dimethylbutane as product.

2. A process according to claim 1 comprising the additional step of passing at least a portion of said overhead separated in (f) to an alkylation zone and alkylating isobutane therein with ethylene to produce diisopropyl.

3. A process according to claim 1 wherein at least a portion of said bottoms separated in (b) is removed for further use as desired to prevent normal butane build-up in the system.

4. A process according to claim 1 wherein said bottoms separated in (f) is deoiled to remove heavies prior to hydrogenation.

5. A process according to claim 1 wherein at least a portion of said overhead separated in (f) is subjected to further fractionation to separately recover an overhead stream comprising $C_2$ and bottoms stream comprising $iC_4$.

6. A process according to claim 5 comprising the additional step of passing at least a portion of said overhead separated in (f) to an alkylation zone and alkylating isobutane therein with ethylene to produce diisopropyl.

7. A process of preparation of high octane diisopropyl (2,3-dimethylbutane) from a mixed butenes feedstream comprising isobutane, isobutylene, butene-1, n-butane and butenes-2 wherein said process comprises the steps (a) passing said feedstream to a double bond isomerization zone and therein subjecting same to isomerization conditions sufficient to convert butene-1 to butenes-2;

(b) separating the effluent from (a) in a first fractionation zone into an overhead stream comprising $C_2$ and $C_3$, a side stream rich in isobutylene, and a bottoms stream rich in butenes-2;

(c) subjecting at least a portion of said bottoms in (b) to olefin skeletal isomerization in a skeletal isomerization zone under conditions suffient to convert butenes-2 to isobutylene and some butene-1;

(d) passing the effluent from (c) as part of the feed to said first fractionation zone in (b);

(e) passing another portion of said bottoms separated in (b) to a cleavage zone or disproportionation zone wherein butenes-2 are converted to propylene in the presence of ethylene;

(f) charging the effluent removed from (e) to a rectification zone operated under conditions to separate an overhead stream comprising ethylene, a side stream comprising propylene, and a bottoms stream comprising isobutane and n-butane;

(g) isomerizing said side stream separated in (b) in a double bond hydroisomerization zone under conditions to convert butene-1 to butenes-2;

(h) subjecting the effluent removed from (g) which is rich in isobutylene and lean in butene-1 to a disproportionation zone (triolefin process) to convert isobutylene to $C_2$ and 2,3-dimethylbutene-2 and butenes-2 to $C_2$ and n-hexene and heavier olefinic hydrocarbons;

(i) passing the effluent from (h) to a deisobutanizer fractionation zone to be operated under conditions to separate an overhead stream comprising isobutane, a side stream comprising isobutylene, and a bottoms steam comprising 2,3-dimethylbutene-2 and small amounts of pentenes-2, hexenes-3 and 2-methylpentene-2;

(j) separating 2,3-dimethylbutene-2-from said bottoms stream; and (k) hydrogenating the fraction separated in (f) to form 2,3-dimethylbutane (DIP) as a product of the process.

8. A process according to claim 7 wherein said bottoms stream (i) is passed to fractionation and subjected to conditions so as to remove an overhead stream comprising pentenes, a side stream comprising hexenes and a bottoms streeam comprising 2,3-diemthylbutene-2 which bottoms stream is then subjected to hydrogenation in step (k) to produce 2,3-dimethylbutane.

9. A process according to claim 7 wherein said side stream comprising isobutylene separated in step (i) is recycled as part of the feed to fractionation step (b), said overhead separated in step (b) is passed as part of the feed to said rectification zone in (f) and the remaining portion of said bottoms removed in step (b) is passed to alkylation.

10. A process according to claim 7 wherein said side stream separated in step (f) is passed to olefin disproportionation to convert propylene to ethylene and butenes-2 and the product thus produced is passed as part of the feed to fractionation in step (b).

11. A process according to claim 7 wherein said overhead separated in step (f) is, in part passed as the source of ethylene for said disproportionation zone in step (e).

12. A process according to claim 7 wherein said bottoms stream (i) is passed to fractionation and subjected to conditions so as to remove an overhead stream comprising pentenes, a side stream comprising hexenes, a bottoms stream comprising 2,3-dimethylbutene-2, which bottoms stream is then subjected to hydrogenation in step (k) to produce 2,3-dimethylbutane and wherein said side stream comprising isobutylene separated in step (i) is recycled as part of the feed to fractionation step (b), said overhead separated in step (b) is passed as part of the feed to said rectification zone in (f) and the remaining portion of said bottoms removed in step (b) is passed to alkylation.

13. A process according to claim 7 wherein said side stream separated in step (f) is passed to olefin disproportionation to convert propylene to ethylene and butenes-2 and the product thus produced is passed as part of the feed to fractionation in step (b) and wherein said overhead separated in step (f) is, in part, passed as the source of ethylene for said disproportionation zone in step (e).

* * * * *